United States Patent [19]

Wilms et al.

[11] 4,410,743
[45] Oct. 18, 1983

[54] PROCESS FOR THE PREPARATION OF 2,3-DIMETHYLBUTANE-2,3-DIOL

[75] Inventors: Klaus G. Wilms, Dormagen; Helmut Waldmann; Johann Grolig, both of Leverkusen, all of Fed. Rep. of Germany

[73] Assignee: Bayer Aktiengesellschaft, Leverkusen, Fed. Rep. of Germany

[21] Appl. No.: 364,344

[22] Filed: Apr. 1, 1982

[30] Foreign Application Priority Data

Apr. 24, 1981 [DE] Fed. Rep. of Germany ....... 3116294

[51] Int. Cl.$^3$ ...................... C07C 31/20; C07C 29/03
[52] U.S. Cl. .................................................. 568/860
[58] Field of Search ........................................ 568/860

[56] References Cited

U.S. PATENT DOCUMENTS 2,644,837  7/1953  Schweitzer .......................... 568/860
3,232,957  2/1966  Sharp .................................. 568/860

FOREIGN PATENT DOCUMENTS 53-65807  6/1978  Japan .................................... 568/860
950669   2/1964  United Kingdom ................ 568/860
458231   9/1977  U.S.S.R. .............................. 568/860

OTHER PUBLICATIONS

Lange, "Handbook of Chemistry", 10th Ed. (1961), pp. 660–661.

Primary Examiner—J. E. Evans
Attorney, Agent, or Firm—Sprung, Horn, Kramer & Woods

[57] ABSTRACT 2,3-Dimethylbutane-2,3-diol is prepared by a process in which 2,3-dimethylbutenes are reacted with oxygen or an oxygen-containing gas, in the presence of 0.01 to 20 parts by weight of water (relative to 2,3-dimethylbutenes employed), at temperatures of from 40° to 180° C. and residence times of 5 to 150 minutes, without the addition of catalysts.

20 Claims, No Drawings

PROCESS FOR THE PREPARATION OF 2,3-DIMETHYLBUTANE-2,3-DIOL

The present invention relates to a process for the preparation of 2,3-dimethylbutane-2,3-diol from 2,3-dimethylbutenes and oxygen or oxygen-containing gases.

2,3-Dimethylbutane-2,3-diol is an important intermediate product which can be used, for example, for rubber syntheses (see Römpps Chemie Lexikon, Stuttgart 1972, page 2701).

A number of processes for the preparation of 2,3-dimethylbutane-2,3-diol have already been disclosed, all of which, however, are unsatisfactory.

Thus, 2,3-dimethylbutane-2,3-diol can be prepared by the reduction of acetone. This reduction can be carried out with magnesium in the presence of mercury chloride (see R. E. W. Adams, Org. Synth. 5, 87; Coll. Vol. I (1956) 459), with aluminum amalgam or electrochemically (see German Pat. No. 306,304 and 310,023). If reactions are carried out in the presence of mercury or mercury compounds, their toxicity and the formation of mercury-containing by-products are disadvantages (see Beilstein, E II, 1, 553). In the case of the reduction with aluminum amalgam, isopropyl alcohol is formed, in addition, as a by-product (see L. F. and M. Fieser, Organische Chemie (Organic Chemistry), Verlag Chemie, Weinheim (1965), page 509) and the electrochemical reduction is very consumptive of energy.

Another process also uses acetone as the starting compound, which is converted photochemically, in the presence of hydrogen donors (for example isopropanol), into 2,3-dimethylbutane-2,3-diol (see G. O. Schenk, Dechema-Monographie 24, 105 (1955)). However, the yield is only 4% of theory after a reaction time of 24 hours (see Houben-Weyl, Methoden der organischen Chemie (Methods of Organic Chemistry), volume VI/Ia, part 2, Georg Thieme Verlag Stuttgart (1980), page 1499).

Further processes use 2,3-dimethylbutenes as starting compounds. Thus, the preparation of 2,3-dimethylbutane-2,3-diol from 2,3-dimethyl-2-butene by treatment with aqueous potassium permanganate solution is described (see Couturier, Annales de Chimie et de Physique, 6th series, 26, (1882), page 479). However, owing to the use of potassium permanganate, this is not a favourable method for preparing 2,3-dimethylbutane-2,3-diol on an industrial scale.

It is also known that 2,3-dimethylbutenes can be converted, by reaction with hydrogen peroxide and formic acid, into 2,3-dimethylbutane-2,3-diol (German Auslegeschrift No. 2,844,637). The selectivity of the diol formation is only approximately 66% relative to the hydrogen peroxide employed, that is to say 34% of the expensive hydrogen peroxide employed does not contribute to the diol formation. By using formic acid, which is a very corrosive agent, problems of corrosion occur. In this process, in addition, the monoformate of 2,3-dimethylbutane-2,3-diol is first formed, from which the diol can be obtained only by hydrolysis with aqueous alkali metal hydroxide. This is therefore a multistage process which has the additional disadvantage that waste liquors which contain alkali metal formates are produced in the hydrolysis.

Furthermore, it is recorded that a mixture of 2,3-dimethyl-2,3-epoxy-butane, 2,3-dimethyl-3-hydroxybut-1-ene and 2,3-dimethyl-3-hydroperoxybut-1-ene can be obtained in the reaction of 2,3-dimethyl-2-butene (=tetramethylethyelene) with oxygen, in the presence of trans-MCl(CO)(Ph$_3$P)$_2$ (M=rhodium or iridium, Ph=phenyl) as the catalyst (see J. Org. Chem. 37, 2881 to 2884 (1972)). The formation of 2,3-dimethylbutane-2,3-diol does not occur. Virtually no conversion of 2,3-dimethyl-2-butene takes place without a catalyst (see ibid. page 2882, Table I, 1st line).

Finally, it is known from Japanese Preliminary Published Application 65,087/78 (=Japanese Patent Application No. 140,890/76) that diols can be prepared by a process in which a mono-olefinic hydrocarbon fraction is oxidized, in the liquid phase, with oxygen or an oxygen-containing gas, in the presence of 0.7 to 8 times the quantity by weight of water (relative to the hydrocarbon fraction), at temperatures of from 80° to 200° C. and pressures of from 5 to 100 kg/cm$^2$. In this process, the reaction times are over 6 and up to 13 hours, and good results are only obtained if catalysts are added. 2,3-Dimethylbutenes have not been subjected to this process, and in view of the above mentioned reference J. Org. Chem. 37, 2881 to 2884, it was not to be expected that 2,3-dimethylbutenes could be converted, using oxygen, into 2,3-dimethylbutane-2,3-diol.

The need for a simple and effective process for the preparation of 2,3-dimethylbutane-2,3-diol thus still existed.

SUMMARY OF INVENTION

A process for the preparation of 2,3-dimethylbutane-2,3-diol has now been found which is characterised in that 2,3-dimethylbutenes are reacted with oxygen or an oxygen-containing gas in the presence of 0.01 to 20 parts by weight of water (relative to 2,3-dimethylbutenes employed), at temperatures of from 40° to 180° C. and residence times of from 5 to 150 minutes. The process can be carried out without the addition of catalysts.

2,3-Dimethyl-2-butene, 2,3-dimethyl-1-butene, any desired mixtures of 2,3-dimethyl-2-butene and 2,3-dimethyl-1-butene, and any desired mixtures of 2,3-dimethyl-2-butene and/or 2,3-dimethyl-1butene, together with inert solvents, are examples of 2,3-dimethylbutenes suitable for use in the process according to the invention. Such inert solvents can, for example, be hydrocarbons and chlorinated hydrocarbons of the aliphatic, cycloaliphatic and aromatic series, for example saturated aliphatic hydrocarbons, such as n-hexane or dimethylbutane, saturated cycloaliphatic hydrocarbons, such as decalin, aromatic hydrocarbons, such as benzene, toluene or xylene, or chlorinated hydrocarbons, for example chlorinated aromatics. Such inert solvents are preferably n-hexane, dimethylbutane, benzene or chlorinated hydrocarbons.

2,3-Dimethyl-2-butene and 2,3-dimethyl-1-butene are readily obtainable starting materials which can be obtained, for example, by the dimerization of propylene (see Houben-Weyl, Methoden der organischen Chemie (Methods of Organic Chemistry), volume V/Ib, page 550 to 551, Stuttgart (1972)) and can be employed in the process according to the invention immediately or, if appropriate, after preliminary distillation. 2,3-Dimethylbutenes, which can be employed in the process according to the invention, can also be obtained by dehydration of 2,3-dimethylbutane-2-ol.

2,3-Dimethyl-2-butene or mixtures of the abovementioned type which contain 2,3-dimethyl-2-butene are preferably employed in the process according to the invention, these mixtures containing over 60%, preferably over 70%, 2,3-dimethyl-2-butene.

The oxygen can be fed as pure oxygen or in the form of an oxygen-containing gas mixture to the process according to the invention. If an oxygen-containing gas mixture is employed, this mixture preferably contains, in addition to oxygen, only further inert constituents. Such inert constituents can, for example, be nitrogen, carbon dioxide and/or noble gases, such as helium, neon, argon and/or krypton. It is also possible to use an inert gas mixture of carbon dioxide and nitrogen, which mixture can be prepared, for example, by the combustion of methane with air, as the inert constituent of the oxygen-containing gas mixture. Additions of ozone or atomic oxygen are also possible.

The oxygen-containing gas mixtures preferably contain between 10 and over 99% of oxygen. Air, oxygen-containing gas mixtures which contain over 50% of oxygen, or pure oxygen are preferably used in the process according to the invention.

It is advantageous that the oxygen to be employed be fed in successively in several portions, for example by forcing in oxygen and/or oxygen-containing gases several times during the reaction.

If an oxygen-containing gas mixture is employed, the various components of the gas mixture can be fed into the reaction zone together, separately or combined in suitable combinations. The mixing of the gas components can be effected inside or outside the reaction zone. The mixing of the gas components outside the reaction zone can be effected, for example, in free jets, in channels, in mixing apparatuses or in mixing chambers. Injector mixers and jet mixers, for example, are suitable. Stirring devices can also be employed for mixing the gases. Blowers can also be used simultaneously with the mixing equipment.

The process according to the invention is carried out in the presence of 0.01 to 20 parts by weight of water (relative to 1 part by weight of 2,3-dimethylbutenes employed). Preferably 0.1 to 15, particularly preferably 0.2 to 10, parts by weight of water are employed, relative to 1 part by weight of 2,3-dimethylbutenes employed. In special cases, more or less than the quantities of water indicated can also be employed.

The water can be fed into the reaction zone in liquid or vapour form. The water is preferably added as a liquid. Furthermore, it is preferably to use demineralized water in order to avoid corrosion problems. However, it is also possible to use water which has not been demineralized or which has been only partially demineralized, for example so-called industrial water, in suitable apparatuses. In many cases it is advantageous to use water to which basic compounds have been added, for example if the formation of acid by-products is observed during the reaction. Suitable basic compounds are, for example, alkali metal and/or alkaline earth metal carbonates, bicarbonates, oxides and hydroxides, such as sodium bicarbonate, calcium carbonate, potassium hydroxide and magnesium oxide, but also organic basic compounds, for example amines.

The process according to the invention is carried out at temperatures of from 40° to 180° C. It is preferably carried out at 60° to 160° C., particularly preferably at 80° to 140° C.

In addition to the procedure under isothermal conditions, that is to say maintaining a uniform temperature during the total reaction, the reaction can also be carried out with the formation of a so-called temperature gradient, that is to say with the temperature increasing or decreasing during the course of the reaction.

The process according to the invention is carried out in such a manner that the residence time (for a discontinuous procedure) or the average residence time (for a continuous procedure) is 5 to 150 minutes. This time is preferably 8 to 120 minutes, particularly preferably 10 to 70 minutes. Within these limits the residence time is relatively long if oxygen or oxygen-containing gas is supplied in several portions.

The process according to the invention is carried out without the addition of catalysts.

In the process according to the invention, the pressure can vary within wide limits. The process can be carried out, for example, at a system pressure of from 0.9 to 90 bars. This pressure is preferably 2.0 to 70 bars, particularly preferably 5.0 to 50 bars. In special cases, it is also possible to fall below or to exceed the pressure ranges indicated. The pressure is preferably established by forcing in the oxygen or the oxygen-containing gas under the appropriate pressure. It is advantageous to force in oxygen or oxygen-containing gas several times during the reaction.

Furthermore, it is advantageous to provide for thorough intermixing of the reaction components during the course of the reaction, for example by intensive stirring or by using a gas dispersion stirrer.

The process according to the invention can be carried out, within the parameters indicated, in such a manner that the conversion of 2,3-dimethylbutenes can vary within wide limits, for example between 1 to 95%. At the end of the reaction, this conversion is preferably 20 to 90%, particularly preferably 30 to 85%.

For 2,3-dimethylbutene conversions of 30 to 85%, 2,3-dimethylbutane-2,3-diol selectivities of 70 to 80%, for example, are achieved by the process according to the invention. The process according to the invention can also be carried out with 2,3-dimethylbutene conversions of greater than 85% but the 2,3-dimethylbutane-2,3-diol selectivity decreases somewhat for higher conversions, under certain circumstances.

The process according to the invention can be carried out both in the liquid phase and in the gas phase. It is preferably carried out in the liquid phase.

The process according to the invention can be carried out discontinuously or continuously in apparatuses customary for reactions of this type. For example, stirred vessels, boiling reactors, tube reactors, twin-loop reactors, loop reactors, stirred vessel cascades and bubble columns are suitable.

Various materials can be used as materials for the apparatuses for carrying out the process according to the invention. For example, glass, stainless steel, nickel alloys, zirconium, tantalum and enamelled materials are suitable.

The heat of reaction can be led away in various ways, for example by internally or externally located condensers or by boiling under reflux, for example in boiling reactors.

The 2,3-dimethylbutenes or mixtures containing them can be introduced in various ways into the apparatus provided for the reaction. They can be fed into the reaction zone together with or separately from the water. Furthermore, it is possible to feed the 2,3-dimethylbutenes, or mixtures containing them, and the water into the reaction zone at different points. When using several reactors arranged as a cascade, it can be advantageous to feed in the 2,3-dimethylbutenes or mixtures containing them exclusively to the first reactor. However, their addition can also be distributed over various reactors or over all the reactors.

When using several reactors arranged as a cascade, oxygen or gas mixtures containing oxygen and/or water can be introduced separately or together into each or into only some of the vessels of the cascade.

The working-up of the reaction mixtures present after the process according to the invention has been carried out, and separating off the 2,3-dimethylbutane-2,3-diol obtained, can be effected in various ways. If the reaction has been carried out at temperatures above the boiling point (at normal pressure) of the 2,3-dimethylbutenes and at elevated pressure, it is advantageous firstly to cool the mixture to temperatures below the boiling point (at normal pressure) of the 2,3-dimethylbutenes, to release the pressure and then to separate off the 2,3-dimethylbutane-2,3-diol. In some circumstances, it is advantageous to release the pressure whilst introducing inert gases, such as nitrogen, carbon dioxide or noble gases, in order to exclude the formation of explosive gas mixtures. The gas mixture liberated when the pressure is released can be recycled into the reaction, if desired after purification and enrichment with oxygen.

After the pressure has been released, the reaction mixture can, for example, firstly be cooled to temperatures above the melting point of 2,3-dimethylbutane-2,3-diol hydrate, that is to say to temperatures above approximately 48° C., for example to 50° to 70° C., preferably to 50° to 60° C., particularly preferably to 50° to 55° C., and a liquid two-phase mixture can thus be obtained, an upper organic phase which essentially contains unreacted 2,3-dimethylbutenes and a lower aqueous phase which essentially contains 2,3-dimethylbutane-2,3-diol and water. The organic phase thus obtained can be recycled into the reaction, if appropriate after it has been completely or partially fed to a distillation stage for concentrating the 2,3-dimethylbutenes. This concentration can also be effected by rectification, for example in a tray column. The distillation or rectification can be effected at normal pressure, elevated pressure or reduced pressure. The resulting aqueous phase can then be further cooled, for example to temperatures below 48° C. to −10° C., preferably to 30° to −5° C., particularly preferably to 20° to 0° C. This cooling can be effected in various ways, for example by external cooling or by vacuum cooling, for example in the form of a vacuum crystallization. The 2,3-dimethylbutane-2,3-diol hydrate which separates out in crystalline form in this process, if appropriate after seeding, can be separated off in any desired manner, for example by filtration, decanting, sedimentation, centrifuging or pressing out. The residual mother liquor can be completely or partially recycled into the reaction, if appropriate after the addition of fresh water, if appropriate after distilling off organic constituents which are lower-boiling than water, and if appropriate after neutralization and/or purification with an ion exchanger.

For example, the reaction mixture can, after the pressure has been released or also directly, be cooled to temperatures below the melting point of 2,3-dimethylbutane-2,3-diol hydrate, that is to say to temperatures below approximately 48° C., and crystalline 2,3-dimethylbutane-2,3-diol hydrate and at least one, if appropriate also two, liquid phases can thus be obtained. The 2,3-dimethylbutane-2,3-diol hydrate can be separated off as described above. A liquid phase essentially containing unreacted 2,3-dimethylbutenes remains as the mother liquor if the available water is completely consumed for the formation of 2,3-dimethylbutane-2,3-diol hydrate. If more water is present, a mother liquor remains which contains a further aqueous phase in addition to the organic phase essentially containing unreacted 2,3-dimethylbutenes. The organic, and if appropriate the aqueous, phase, if appropriate after separation into an organic and an aqueous phase, can be further worked up, as described above, and recycled into the reaction.

The 2,3-dimethylbutane-2,3-diol hydrate thus obtained can already be used as such for many purposes, for example for the rearrangement in pinacolone (see, for example, Römpps Chemie Lexikon, Stuttgart 1974, page 2702). If desired, 2,3-dimethylbutane-2,3-diol can be obtained from the 2,3-dimethylbutane-2,3-diol hydrate by separating off water. Separating off the water of hydration can be effected, for example, by azeotropic dehydration.

The process according to the invention makes possible a simple and economical preparation of 2,3-dimethylbutane-2,3-diol. High selectivities of reaction can be achieved, the use of hydrogen peroxide, which is expensive in comparison with oxygen or air, is avoided, catalysts are not required and the reaction times are short.

It is decidedly surprising that these advantages can be realised with the process according to the invention, since, in view of the reference described at the beginning, namely J. Org. Chem. 37, 2881 to 2884 (1972), and from Japanese Preliminary Published Application 65,087/78, it was not to be expected that 2,3-dimethylbutane-2,3-diol can be prepared without catalysts and with short reaction times.

The process according to the invention is illustrated by the examples which follow, without being limited to them. If not stated to the contrary, all percentage data represent percentages by weight.

EXAMPLE 1

255 g of a mixture consisting of 98% of 2,3-dimethyl-2-butene, 1% of 2,3-dimethyl-1-butene and 1% of n-hexane, as well as 108 g of water, were introduced into a stainless steel autoclave which was provided with a mechanical stirrer, a thermometer and a valve. The autoclave was warmed to 100° C. whilst stirring (400 rpm). Whilst the mixture was further stirred, air at 25 bars was forced in and the mixture was stirred for a further 15 minutes at 100° C. The autoclave was then cooled to room temperature, whilst stirring, and the reaction products were analysed. The evaluation gave 3% 2,3-dimethylbutene conversion with 89% selectivity, relative to 2,3-dimethylbutane-2,3-diol prepared.

EXAMPLE 2

The procedure of Example 1 was followed, but the autoclave was warmed only to 80° C. Oxygen at 5 bars was forced in fifteen times at intervals of 10 minutes, whilst stirring (400 rpm). After a further 15 minutes, the autoclave was cooled to room temperature and the reaction products were analysed. The evaluation gave 35% 2,3-dimethylbutene conversion with 78% selectivity, relative to 2,3-dimethylbutane-2,3-diol prepared.

EXAMPLE 3

312 g of a mixture consisting of 90% of 2,3-dimethyl-2-butene, 8.5% of 2,3-dimethyl-1-butene and 1.5% of 2,3-dimethylbutane, as well as 58 g of an aqueous potassium carbonate solution with a pH value of 9, were introduced into the autoclave described in Example 1. After the mixture had been warmed to 50° C., a gas mixture, at 80 bars, consisting of 10% of oxygen and 90% of carbon dioxide, was forced in whilst stirring (600 rpm), and the mixture was further stirred for 30 minutes. After the mixture had been cooled to room temperature, the reaction products were analysed. The evaluation gave 1.8% 2,3-dimethylbutene conversion with 72% selectivity, relative to 2,3-dimethylbutane-2,3-diol prepared.

EXAMPLE 4

51 g of a mixture consisting of 80% of 2,3-dimethyl-2-butene, 15% of 2,3-dimethyl-1-butene, 2% of 2,3-dimethylbutane and 3% of n-hexane, as well as 412 g of water, were introduced into the autoclave described in Example 1. After the mixture had been heated up to 125° C., a gas mixture, at 20 bars, consisting of 50% of oxygen and 50% of nitrogen, and, after a further 5 minutes, pure oxygen at 3 bars were forced in whilst stirring (1,000 rpm). The mixture was further stirred for 10 minutes at 125° C. The autoclave was cooled to room temperature and the reaction products were analysed. The evaluation gave 41% 2,3-dimethylbutene conversion with 65% selectivity, relative to 2,3-dimethylbutane-2,3-diol prepared.

EXAMPLE 5

208 g of a mixture consisting of 95% of 2,3-dimethyl-2-butene, 3% of 2,3-dimethyl-1-butene, 1.5% of 2,3-dimethylbutane and 0.5% of n-hexane, as well as 83 g of water, were introduced into the autoclave described in Example 1. After the mixture had been warmed to 117° C. oxygen at 2.5 bars in each case was forced in 10 times, at intervals of 10 minutes, whilst stirring (680 rpm), and the mixture was then further stirred for 5 minutes. After the autoclave had been cooled to 50° C. and the pressure had been released via a cold trap cooled to −70° C., two liquid phases were obtained and were separated. After distillation, the organic phase was again employed for the oxidation with oxygen. The aqueous phase was cooled to +8° C. and the 2,3-dimethylbutane-2,3-diol hydrate which separated out after seeding was separated off by centrifuging. The evaluation of the experiment gave 16.3% 2,3-dimethylbutene conversion with 77% selectivity, relative to 2,3-dimethylbutane-2,3-diol prepared.

EXAMPLE 6

The procedure of Example 5 was followed, but the autoclave was cooled to 15° C. after the last batch of oxygen at 2.5 bars had been forced in. After the pressure had been released via a cold trap cooled with dry ice, the reaction mixture was separated, by filtration, into solid and liquid constituents, the solid thus obtained being crystalline 2,3-dimethylbutane-2,3-diol hydrate. The liquid constituents were separated in a phase separator into two liquid phases. The organic phase, after rectification in a bubble tray column, and the aqueous phase, after distilling off organic constituents which are lower-boiling than water, were recycled into the reaction zone for further reaction. The evaluation of the experiment gave 14.7% 2,3-dimethylbutene conversion with 75% selectivity, relative to 2,3-dimethylbutane-2,3-diol prepared.

EXAMPLE 7

700 g/hour of a mixture consisting of 97% of 2,3-dimethyl-2-butene, 1.3% of 2,3-dimethyl-1-butene, 0.8% of 2,3-dimethylbutane and 0.9% of n-hexane, as well as 230 g/hour of water, were introduced into a cascade consisting of 4 stirred pressure reactors of 300 ml capacity each. The first and second reactors of the cascade were operated at 120° C., the third at 115° C. and the fourth at 110° C. After the prescribed reaction temperatures had been reached, a quantity of oxygen was forced into each reactor, via a valve, such that the total pressure in the cascade was 12 bars. The reaction mixture was depressurized, after the cascade, with the addition of nitrogen in order to exclude explosive gas mixtures. The reaction mixture was then cooled to 52° C. and was separated in a separator into two liquid phases. The organic phase was recycled into the first reactor of the cascade, after rectification in a sieve tray column to concentrate unreacted 2,3-dimethylbutenes and after addition of fresh 2,3-dimethylbutene mixture. The aqueous phase was cooled to 12° C. in vacuo, whilst simultaneously distilling off organic constituents which were lower-boiling than water. The 2,3-dimethylbutane-2,3-diol hydrate which separated out in crystalline form after seeding was separated off by centrifuging. The organic constituents which had been distilled off were fed to a biological clarification. The residual aqueous mother liquor was recycled into the process, after addition of fresh water.

The analytical evaluation gave 12% 2,3-dimethylbutene conversion with a selectivity of 73%, relative to 2,3-dimethylbutane-2,3-diol hexahydrate prepared. 162 g of crystalline 2,3-dimethylbutane-2,3-diol hexahydrate were obtained per hour.

EXAMPLE 8

255 g of a mixture consisting of 98% of 2,3-dimethyl-2-butene, 1% of 2,3-dimethyl-1-butene and 1% of n-hexane, as well as 108 g of water, were introduced into a stainless steel autoclave which was provided with a gas dispersion stirrer, a thermometer and a valve. The autoclave was warmed to 120° C. whilst stirring (1000 rpm). Whilst the mixture was further stirred, air at 26 bars was forced in and the mixture was stirred for further 15 minutes at 120° C. During this period, the amount of oxygen consumed was continuously supplemented. The autoclave was then cooled to room temperature, whilst stirring, and the reaction products were analyzed. The evaluation gave 83% 2,3-dimethylbutene conversion with 78% selectivity, relatively to 2,3-dimethylbutane-2,3-diol prepared.

EXAMPLE 9

255 g of a mixture consisting of 98% of 2,3-dimethyl-2-butene, 1% of 2,3-dimethyl-1-butene and 1% of n-hexane, as well as 108 g of water, were introduced into a stainless steel autoclave which was provided with a gas dispersion stirrer, a thermometer and a valve. The autoclave was warmed to 110° C. whilst stirring (2.000 rpm). Whilst the mixture was further stirred, air at 28 bars was forced in and the mixture was stirred for further 30 minutes at 110° C. During this period, the amount of oxygen consumed was continuously supplemented. The autoclave was then cooled to room temperature, whilst stirring, and the reaction products were analyzed. The evaluation gave 93% 2,3-dimethylbutene conversion with 76% selectivity, relatively to 2,3-dimethylbutane-2,3-diol prepared.

What is claimed is:

1. A process for the preparation of 2,3-dimethylbutane-2,3diol which comprises contacting 2,3-dimethylbutene with oxygen or an oxygen-containing gas in the presence of 0.01 to 20 parts by weight of water relative to the 2,3-dimethylbutene, at a temperature of from 40° to 180° C. without the addition of a catalyst and in the presence of not more than 5% by weight of an inert organic solvent.

2. A process according to claim 1, wherein the process is conducted at a residence time of from 5 to 150 minutes.

3. A process according to claim 2, wherein the reaction is carried out at a pressure from 0.9 to 90 bars.

4. A process according to claim 2, wherein air, oxygen-containing gas containing over 50% oxygen or pure oxygen is employed as the oxygen-containing gas.

5. A process according to claim 2, wherein oxygen is added successively in several portions.

6. A process according to claim 2, wherein the water employed is one to which at least one basic compound has been added.

7. A process according to claim 2, wherein the process is carried out at a temperature from 60° to 160° C.

8. A process according to claim 2, wherein the reaction mixture is cooled to a temperature below the boiling point of 2,3-dimethylbutenes and the pressure is released.

9. A process according to claim 9, wherein after the pressure has been released the reaction mixture is initially cooled to a temperature above the melting point of 2,3-dimethylbutane-2.3-diol hydrate, a liquid two-phase mixture is obtained, the organic portion of which is recycled to the reaction and the aqueous phase, if any, is cooled to a temperature in the range of below 48° C. to −10° C., the 2,3-dimethylbutane-2,3-diol hydrate which separates out in crystalline form is separated off therefrom and the residual mother liquor is at least partially recycled to the reaction.

10. A process according to claim 8, wherein after the pressure has been released, the reaction mixture is cooled to a temperature below the melting point of 2,3-dimethylbutane-2,3-diol hydrate, crystalline 2,3-dimethylbutane-2,3-diol hydrate is separated off and the mother liquor is recycled into the reaction.

11. A process according to claim 1, wherein water is present in an amount of at least 0.1% by weight relative to the 2,3-dimethylbutene.

12. A process according to claim 11, wherein water is present in an amount of 0.1 to 15 parts by weight relative to the 2,3-dimethylbutene.

13. A process according to claim 1, wherein water is present in an amount of at least 0.2 parts by weight relative to the 2,3-dimethylbutene.

14. A process according to claim 15, wherein water is present in an amount of 0.2 to 10 parts by weight relative to the 2,3-dimethylbutene.

15. A process according to claim 1, wherein the process is carried out employing a reaction mixture consisting essentially of said 2,3-dimethylbutene, said oxygen or said oxygen-containing gas and said water.

16. A process according to claim 1, wherein the process is carried out employing a reaction mixture consisting essentially of said 2,3-dimethylbutene, said oxygen or said oxygen-containing gas, said water and at least one basic compound.

17. A process according to claim 1, wherein said process is performed by adding olefin, oxygen or oxygen-containing gas and water to a reaction vessel maintained under pressure.

18. A process according to claim 17, wherein said water is added from a separate source.

19. A process according to claim 6, wherein said basic compound is an alkali metal or alkaline earth metal carbonate, bicarbonate, oxide or hydroxide.

20. A process according to claim 1, which is carried out without recycling any components remaining in the reaction mixture following completion of the process.

* * * * *